(12) United States Patent
Liao

(10) Patent No.: US 12,599,229 B2
(45) Date of Patent: *Apr. 14, 2026

(54) FLIP-DOWN ELECTRONICS CABINET HAVING CIRCUIT CONTROLLING DEVICE

(71) Applicant: BLUESKY COOKING STYLE CO., LTD., Taipei City (TW)

(72) Inventor: Chin-Jung Liao, Taipei City (TW)

(73) Assignee: BLUESKY COOKING STYLE CO., LTD., Taipei City (TW)

( * ) Notice: Subject to any disclaimer, the term of this patent is extended or adjusted under 35 U.S.C. 154(b) by 134 days.

This patent is subject to a terminal disclaimer.

(21) Appl. No.: 18/624,529

(22) Filed: Apr. 2, 2024

(65) Prior Publication Data

US 2024/0335034 A1 Oct. 10, 2024

(30) Foreign Application Priority Data

Apr. 7, 2023 (TW) ................................. 112112993

(51) Int. Cl.
*H02B 1/38* (2006.01)
*A47B 77/08* (2006.01)
(Continued)

(52) U.S. Cl.
CPC ................ *A47B 77/08* (2013.01); *A61L 9/22* (2013.01); *H05K 7/20172* (2013.01); *A61L 2209/212* (2013.01)

(58) Field of Classification Search
CPC ........... A47B 46/00; A47B 77/08; A61L 9/22; H05K 5/0217; H05K 7/183; H05K 7/20136; H05K 7/20172; H02B 1/0523; H02B 1/38
(Continued)

(56) References Cited

U.S. PATENT DOCUMENTS 1,745,218 A * 1/1930 James .................... A47B 63/02
40/325
3,794,401 A * 2/1974 Dean .................... A47B 46/005
312/331
(Continued)

FOREIGN PATENT DOCUMENTS

TW M569586 U 11/2018
TW M594894 U 5/2020
(Continued)

*Primary Examiner* — James O Hansen
(74) *Attorney, Agent, or Firm* — Li & Cai Intellectual Property (USA) Office

(57) ABSTRACT
A flip-down electronics cabinet includes a cabinet body, two first and two second sliding rails, a carrying tray, a door plate, and a circuit controlling device disposed in the cabinet body. The circuit controlling device includes a control interface, a controller, a master switch circuit, and a first and a second switch circuit. The control interface includes a master switch key, and a first and a second switch key. The controller enters an operation or a standby mode according to a received master switch signal. The master switch circuit is switched off when the controller enters the standby mode, and is switched on when the controller enters the operation mode. After entering the operation mode, the controller respectively controls the first switch circuit and the second switch circuit to be switched on or off according to a first switch signal and a second switch signal received thereby.

6 Claims, 6 Drawing Sheets

(51) Int. Cl.
  *A61L 9/22*            (2006.01)
  *H05K 7/20*            (2006.01)
(58) Field of Classification Search
  USPC ......................................... 312/311, 322, 323
  See application file for complete search history.

(56)                    References Cited

U.S. PATENT DOCUMENTS

| | | | | |
|---|---|---|---|---|
| 3,860,308 | A * | 1/1975 | Burke .................. | A47B 88/493 |
| | | | | 100/229 A |
| 5,242,220 | A * | 9/1993 | Sandreth ................. | B65F 1/004 |
| | | | | D34/1 |
| 5,399,010 | A * | 3/1995 | McClung .............. | E06B 3/5045 |
| | | | | 312/332 |
| 5,520,451 | A * | 5/1996 | Oshima ................. | E05D 15/582 |
| | | | | 312/331 |
| 6,382,749 | B1 * | 5/2002 | Stetson .................. | A47B 81/06 |
| | | | | 312/316 |
| 9,801,302 | B2 * | 10/2017 | Huang ................... | H05K 7/186 |
| 2003/0042828 | A1 * | 3/2003 | Bonin ................... | A47B 67/02 |
| | | | | 220/87.1 |
| 2006/0132006 | A1 * | 6/2006 | Schluter .............. | H05K 5/0226 |
| | | | | 312/323 |
| 2012/0280602 | A1 * | 11/2012 | Baker ................... | A47B 67/04 |
| | | | | 312/236 |
| 2024/0022049 | A1 * | 1/2024 | Liao ........................ | A61L 9/205 |
| 2024/0023286 | A1 * | 1/2024 | Liao ........................ | A47B 77/12 |

FOREIGN PATENT DOCUMENTS

| | | | |
|---|---|---|---|
| TW | M615458 | U | 8/2021 |
| TW | M642693 | U | 6/2023 |

* cited by examiner

FLIP-DOWN ELECTRONICS CABINET HAVING CIRCUIT CONTROLLING DEVICE

CROSS-REFERENCE TO RELATED PATENT APPLICATION

This application claims the benefit of priority to Taiwan Patent Application No. 112112993, filed on Apr. 7, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an electronics cabinet, and more particularly to a flip-down electronics cabinet having a circuit controlling device.

BACKGROUND OF THE DISCLOSURE

As the main location for cooking in every household, the kitchen is where various electric appliances (e.g., electric pots, multi-functional cookers, ovens, microwave ovens, and hot water bottles) are placed. Without proper placement of these electric appliances, the kitchen can quickly become disorganized.

Accordingly, an electronics cabinet that can be used for accommodating the above-mentioned electric appliances is available on the market. In addition, two sockets are disposed inside the electronics cabinet for providing electricity to two electric appliances that are placed in the electronics cabinet and connected to the two sockets. Currently, the most common electric appliance that is placed in the electronics cabinet is a multi-functional cooker of a specific brand, which may be used for a long time and is present in almost every household. There is only one pop-up switch on said multi-functional cooker. The multi-functional cooker begins cooking after the switch is pressed. When the switch pops up, the multi-functional cooker starts to keep the food warm. The multi-functional cooker is unable to be automatically switched off, but keeps warming the food and consuming electricity. When warming of the food is not required, or when the multi-functional cooker needs to be switched off, the only way is to manually remove a plug. In a situation where two electric appliances (e.g., a stewing pot and the multi-functional cooker having only one pop-up switch) are placed in the electronics cabinet, and the multi-functional cooker has finished cooking, the switch of the multi-functional cooker will pop up, and the multi-functional cooker starts to keep the food warm. Nevertheless, the stewing pot still needs to perform cooking for a long period of time (e.g., 4 hours to 6 hours). In order for the multi-functional cooker to stop warming the food and consuming electricity, a user usually needs to put his/her hand into the electronics cabinet that is full of hot air for finding and pulling out the plug of the multi-functional cooker. Such a process can be very inconvenient and dangerous. However, if the user presses a power button on a panel of the electronics cabinet to avoid the inconvenience and danger, the power will stop being supplied to both sockets in the electronics cabinet at the same time, thereby causing the stewing pot to suddenly stop operating. This may inconvenience the user greatly. While the multi-functional cooker of this specific brand cannot be easily discarded due to its durability and usefulness, inconvenience and danger in use may arise when being placed in the electronics cabinet. Therefore, there is still room for improvement on this long existing problem in the related art.

SUMMARY OF THE DISCLOSURE

In response to the above-referenced technical inadequacies, the present disclosure provides a flip-down electronics cabinet having a circuit controlling device.

In order to solve the above-mentioned problems, one of the technical aspects adopted by the present disclosure is to provide a flip-down electronics cabinet having a circuit controlling device. The flip-down electronics cabinet includes a cabinet body, two first sliding rails, two second sliding rails, a carrying tray, a door plate, and the circuit controlling device. The cabinet body includes a top plate, a bottom plate, a rear plate, and two side plates. A first space and a second space are formed between the top plate, the bottom plate, the rear plate, and the two side plates. An opening is formed at a front side of the cabinet body, and the opening is in spatial communication with the first space and the second space. A first socket and a second socket are disposed at a rear side of the cabinet body, and are each exposed from the first space. The two first sliding rails are oppositely disposed on the two side plates of the cabinet body, and the two first sliding rails are disposed in the first space. The two second sliding rails are oppositely disposed on the two side plates of the cabinet body, and the two second sliding rails are disposed in the second space below the first space. A left side and a right side of the carrying tray are respectively disposed on the two first sliding rails. A left side and a right side of the door plate are respectively disposed on the two second sliding rails, and opening and closing actions of the door plate are performable relative to the cabinet body. The circuit controlling device is disposed in the cabinet body, and includes a control interface, a controller, a master switch circuit, a first switch circuit, and a second switch circuit. The controller is electrically connected to the control interface, the master switch circuit, the first switch circuit, and the second switch circuit. The first switch circuit is electrically connected between the master switch circuit and the first socket, and the second switch circuit is electrically connected between the master switch circuit and the second socket. The control interface includes a master switch key, a first switch key, and a second switch key. The master switch key is configured to generate a master switch signal that is transmitted to the controller, the first switch key is configured to generate a first switch signal that is transmitted to the controller, and the second switch key is configured to generate a second switch signal that is transmitted to the controller. The controller is configured to enter an operation mode or a standby mode according to the master switch signal that is received by the controller. The master switch circuit is switched off when the controller enters the standby mode, and the master switch circuit is switched on when the controller enters the operation mode. After the controller enters the operation mode, the controller is configured to respectively control the first switch circuit and the second switch circuit to be switched on or switched off according to the first switch signal and the second switch signal that are received by the controller.

In one of the possible or preferred embodiments, the first switch circuit includes a first left switch and a first right switch that are connected to each other, and the first left switch and the first right switch are each electrically connected to the controller. The second switch circuit includes a second left switch and a second right switch that are connected to each other, and the second left switch and the second right switch are each electrically connected to the controller. The first left switch and the second left switch are semiconductor switches, and the first right switch and the second right switch are relay switches. The controller is configured to quickly switch off the first left switch or the second left switch, and then switch off the first right switch or the second right switch, such that the first switch circuit or the second switch circuit is switched from on to off.

In one of the possible or preferred embodiments, the controller is further configured to continuously record manually switched-off frequencies of the first switch circuit and the second switch circuit, so as to automatically switch off the first switch circuit or the second switch circuit according to a highest one of the manually switched-off frequencies of the first switch circuit and the second switch circuit.

In one of the possible or preferred embodiments, at least one exhaust fan is disposed inside the cabinet body, the circuit controlling device further includes an exhaust fan controlling circuit, and the exhaust fan controlling circuit is electrically connected between the controller and the at least one exhaust fan.

In one of the possible or preferred embodiments, an off-odor cleaning device is disposed inside the cabinet body, and the off-odor cleaning device is electrically connected to the controller. The off-odor cleaning device is a negative ion cleaning device configured to ionize air molecules when the first switch circuit and the second switch circuit are switched off, so as to generate a large amount of negative ions and a minute amount of ozone for neutralization of an off-odor and sterilization of bacteria.

In one of the possible or preferred embodiments, an off-odor cleaning device is disposed inside the cabinet body, and the off-odor cleaning device is electrically connected to the controller. The off-odor cleaning device is a photocatalytic ultraviolet cleaning device configured to irradiate ultraviolet light on a photocatalyst when the first switch circuit and the second switch circuit are switched off, so as to generate oxygen-containing radicals that have a strong oxidizing property for strong oxidative decomposition of an off-odor and bacteria.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
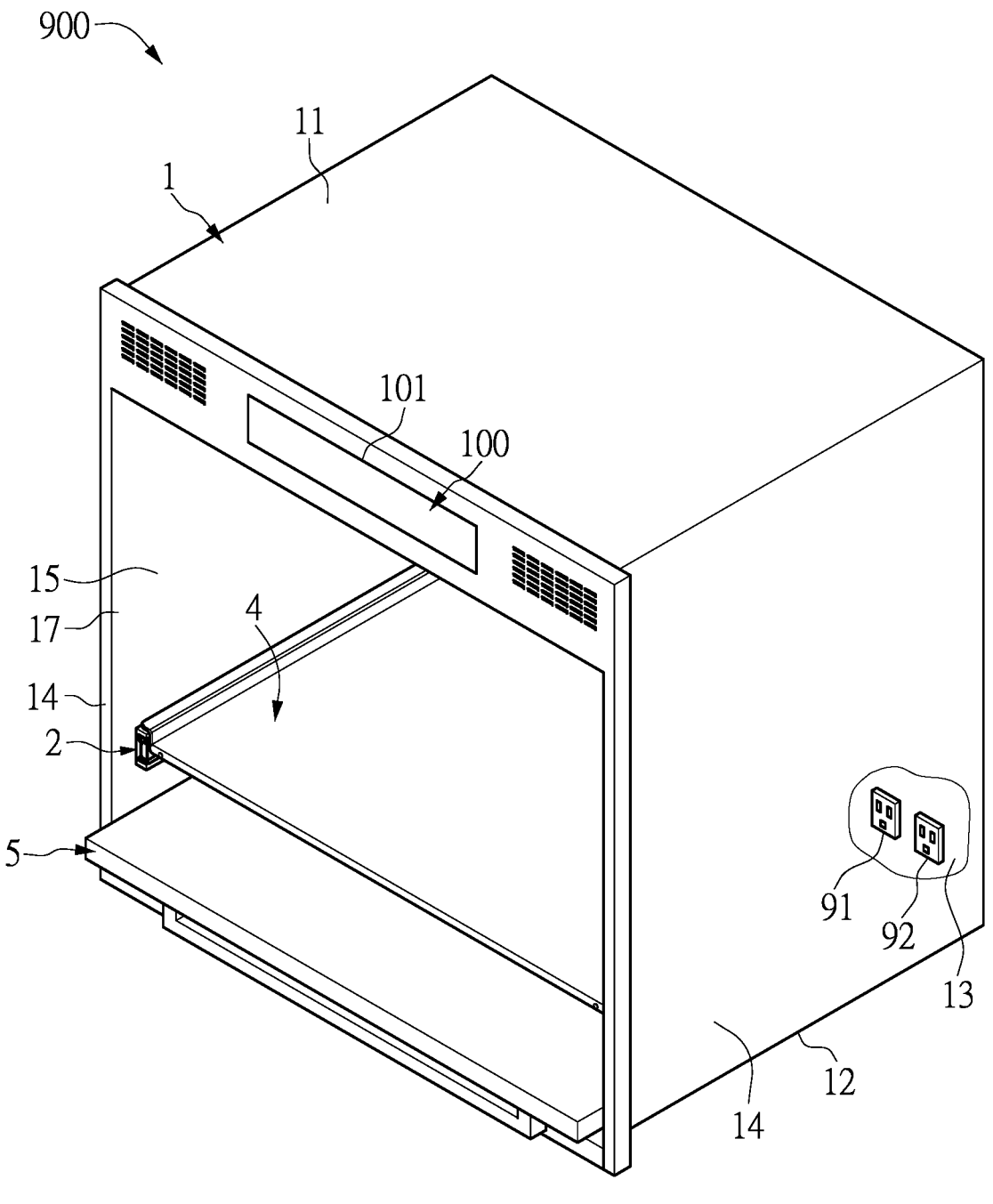
FIG. 1 is a schematic perspective view of a flip-down electronics cabinet having a circuit controlling device according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

EMBODIMENTS

Referring to FIG. 1 to FIG. 4, the present disclosure provides a flip-down electronics cabinet 900 having a circuit controlling device 100. The flip-down electronics cabinet 900 can be used to accommodate electric appliances or other kitchenware, and the flip-down electronics cabinet 900 can be mounted in base cabinets (i.e., cabinets below a kitchen counter), tall cabinets, or a kitchen island. The flip-down electronics cabinet 900 essentially includes a cabinet body 1, two first sliding rails 2, two second sliding rails 3, a carrying tray 4, and a door plate 5.

The cabinet body 1 is preferably square-shaped. The cabinet body 1 includes a top plate 11, a bottom plate 12, a rear plate 13, and two side plates 14, and the top plate 11, the bottom plate 12, the rear plate 13, and the two side plates 14 are connected to each other for formation of a hollow body. Since the structure of the cabinet body 1 is a conventional technology and is not limited in the present disclosure, details thereof will not be elaborated herein.

A first space 15 and a second space 16 are formed inside the cabinet body 1. That is, the first space 15 and the second space 16 can be formed between the top plate 11, the bottom plate 12, the rear plate 13, and the two side plates 14 mentioned above. Preferably, the first space 15 is located above the second space 16, and a first space height H1 is greater than a second space height H2. The first space 15 can be used to accommodate electric appliances, such as a multi-functional cooker, a stewing pot, a microwave oven, and an oven. An opening 17 is formed at a front side of the cabinet body 1, and the opening 17 is in spatial communication with the first space 15 and the second space 16, such that the electric appliances can be placed inside the first space 15 through the opening 17.

The two first sliding rails 2 are oppositely disposed on the two side plates 14 of the cabinet body 1. The two first sliding rails 2 are disposed in the first space 15. Preferably, the two first sliding rails 2 are disposed adjacent to a bottom portion of the first space 15. The two second sliding rails 3 are oppositely disposed on the two side plates 14 of the cabinet body 1, and the two second sliding rails 3 are located below the two first sliding rails 2. The two second sliding rails 3 can be disposed in the second space 16 below the first space 15. Preferably, the two second sliding rails 3 are disposed adjacent to a bottom portion of the second space 16. Since the above-mentioned first sliding rails 2 and second sliding rails 3 are existing sliding rail structures, and the structure of the first sliding rail 2 and the second sliding rail 3 is not limited in the present embodiment, details thereof will not be elaborated herein.

A left side and a right side of the carrying tray 4 are respectively disposed on the two first sliding rails 2, such that the carrying tray 4 is disposed adjacent to the bottom portion of the first space 15. Through guidance of the two first sliding rails 2, the carrying tray 4 can be pulled out or pushed in relative to the cabinet body 1. As such, the carrying tray 4 is movable along a horizontal (front-and-rear) direction within the cabinet body 1, and can be pushed into or pulled out of the cabinet body 1. When the carrying tray 4 is pushed into the cabinet body 1, the carrying tray 4 is located in the first space 15. In this way, the electric appliances can be placed on the carrying tray 4, and accommodation of the electric appliances in the first space 15 of the cabinet body 1 can be achieved by use of the carrying tray 4.

The door plate 5 is a board that corresponds to the opening 17, and can be used to open or close the opening 17. A left side and a right side of the door plate 5 are respectively disposed on the two second sliding rails 3. In the present embodiment, the door plate 5 is a flip-down door plate. That is, the door plate 5 can be flipped downward and slide. When the door plate 5 opens the opening 17, the door plate 5 is disposed adjacent to the bottom portion of the second space 16. Through guidance of the two second sliding rails 3, opening and closing actions of the door plate 5 are performable relative to the cabinet body 1.

In the present embodiment, the door plate 5 includes a door plate front portion 51 and a door plate rear portion 52, and the door plate front portion 51 and the door plate rear portion 52 are pivotally connected to each other by pivotal connection components 53 (such as hinges), such that the door plate front portion 51 and the door plate rear portion 52 are integrally connected. When the door plate front portion 51 and the door plate rear portion 52 move forward, the door plate front portion 51 can upwardly cover the opening 17 of the cabinet body 1, such that the opening 17 of the cabinet body 1 is in a closed state. At this time, the door plate rear portion 52 is still accommodated in the cabinet body 1. When the door plate front portion 51 and the door plate rear portion 52 move rearward, the door plate front portion 51 can be accommodated in the cabinet body 1, such that the opening 17 of the cabinet body 1 is in an open state. Hence, through guidance of the two second sliding rails 3, the door plate 5 can slidably move along a front-and-rear direction, and be accommodated in the cabinet body 1 after being flipped downward.

Figure 2:
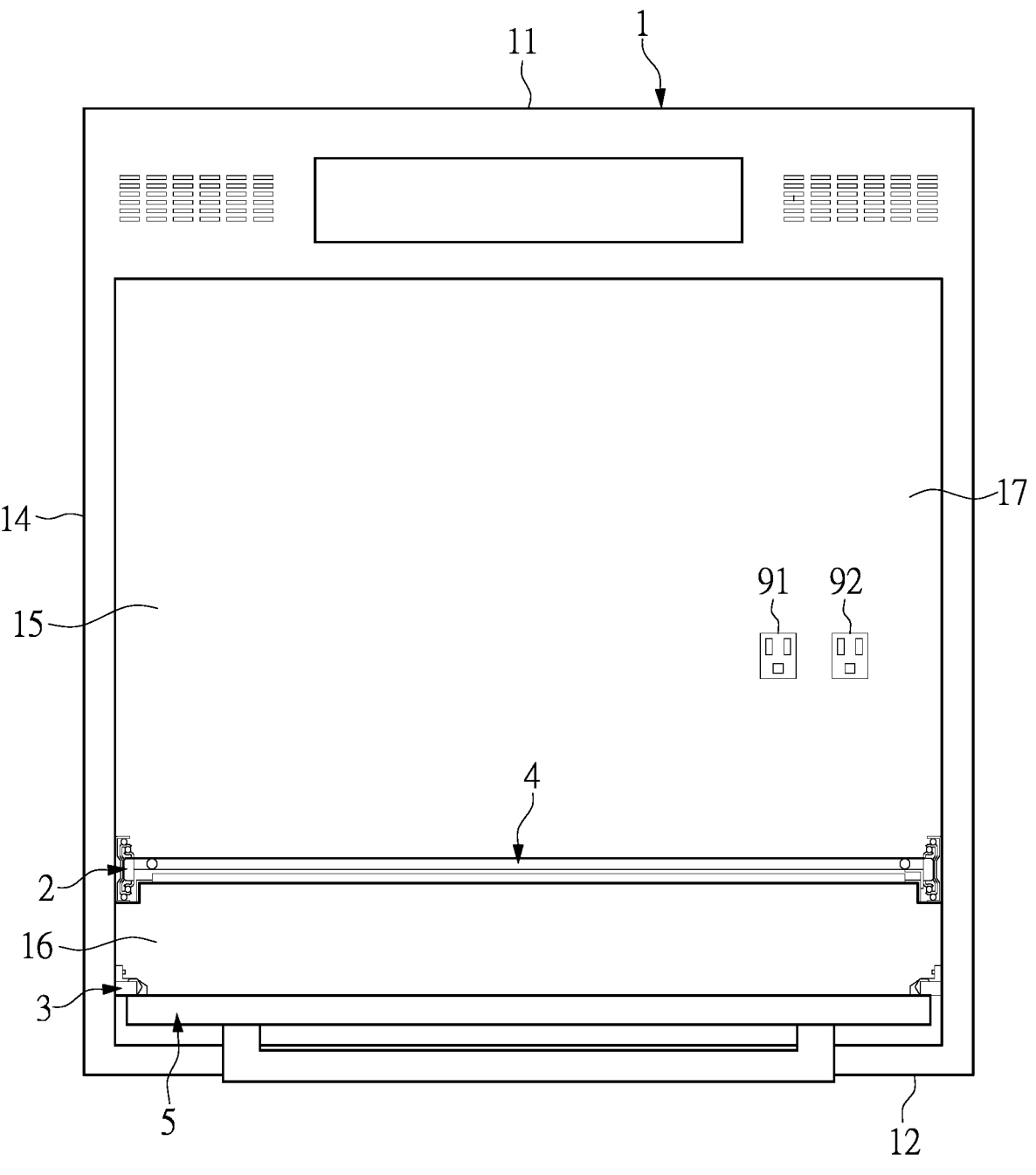
FIG. 2 is a schematic front view of the flip-down electronics cabinet having the circuit controlling device according to the present disclosure.
Figure 3:
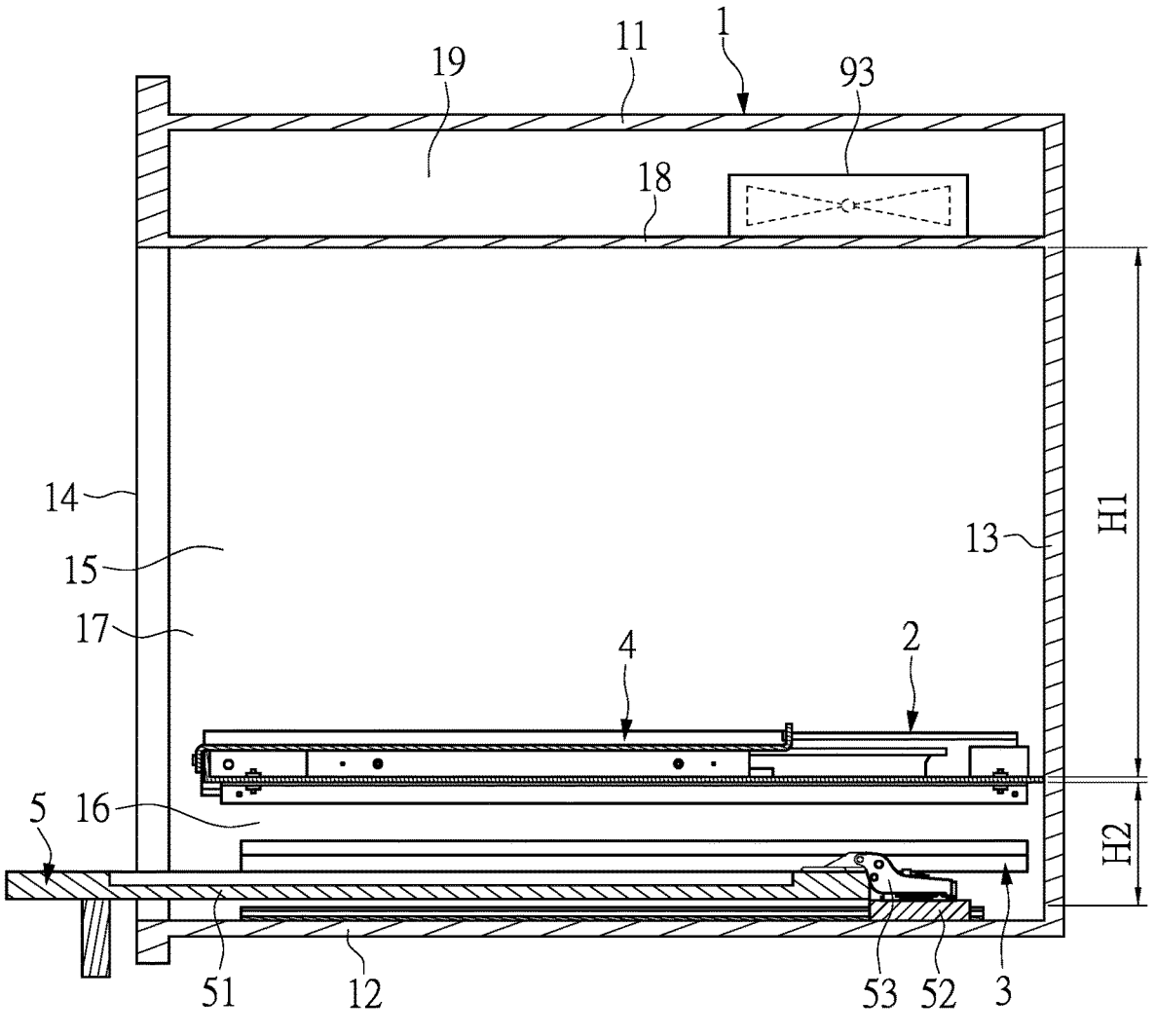
FIG. 3 is a schematic cross-sectional view of the flip-down electronics cabinet having the circuit controlling device according to the present disclosure.

Furthermore, a first socket 91 and a second socket 92 are disposed at a rear side of the cabinet body 1 (as shown in FIG. 1 and FIG. 2). That is, the first socket 91 and the second socket 92 can be disposed on the rear plate 13 of the cabinet body 1, and can each be exposed from the first space 15. As shown in FIG. 3, the cabinet body 1 can further include at least one dividing plate 18 for separating the first space 15 and a mounting space 19, and at least one exhaust fan 93 can be disposed in the mounting space 19.

Figure 4:
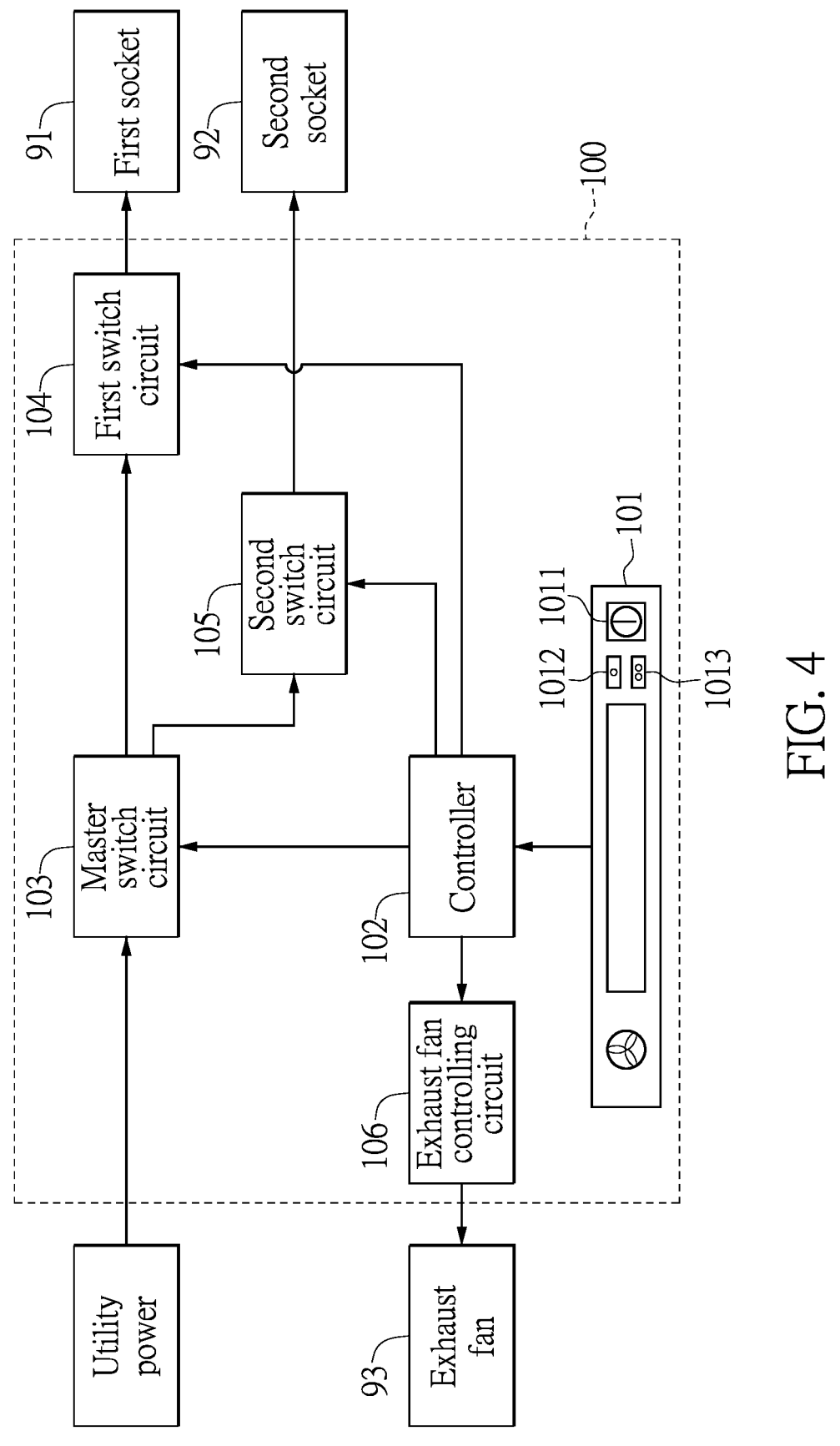
FIG. 4 is a functional block diagram of the flip-down electronics cabinet having the circuit controlling device according to the present disclosure.

The circuit controlling device 100 is disposed on an appropriate location of the cabinet body 1. As shown in FIG. 4, the circuit controlling device 100 essentially includes a control interface 101, a controller 102, a master switch circuit 103, a first switch circuit 104, and a second switch circuit 105. The controller 102 is electrically connected to the control interface 101, the master switch circuit 103, the first switch circuit 104, and the second switch circuit 105. The first switch circuit 104 is electrically connected between the master switch circuit 103 and the first socket 91, and the second switch circuit 105 is electrically connected between the master switch circuit 103 and the second socket 92. In addition, the circuit controlling device 100 can further include an exhaust fan controlling circuit 106 (e.g., a drive circuit or a pulse-width modulation (PWM) circuit), and the exhaust fan controlling circuit 106 is electrically connected between the controller 102 and the exhaust fan 93.

In the present embodiment, the control interface 101 can be, but is not limited to being, exposed from the cabinet body 1 in the form of a control panel. Preferably, the control interface 101 is exposed from the front side of the cabinet body 1. The controller 102, the master switch circuit 103, the first switch circuit 104, the second switch circuit 105, the exhaust fan controlling circuit 106, or relevant active and passive components can be integrated together for formation of a control substrate, and the control substrate is located in the mounting space 19. The controller 102 can also be integrated into the control panel, which may be designed according to practical requirements and is not limited herein.

Specifically, the control interface 101 includes a master switch key 1011, a first switch key 1012, and a second switch key 1013. The master switch key 1011, the first switch key 1012, and the second switch key 1013 can each be a press-type button or a touch-type button, but the present disclosure is not limited thereto. According to the pressing or touching of a user, the master switch key 1011 is configured to generate a master switch signal that is transmitted to the controller 102, the first switch key 1012 is configured to generate a first switch signal, and the second switch key 1013 is configured to generate a second switch signal.

The controller 102 enters an operation mode or a standby mode according to the master switch signal that is received by the controller 102. When the user presses or touches the master switch key 1011, the master switch signal is generated and transmitted to the controller 102, and the controller 102 enters the operation mode from the standby mode.

When the user presses or touches the master switch key 1011 again, the master switch signal is generated and transmitted to the controller 102, and the controller 102 enters the standby mode from the operation mode. Furthermore, the master switch circuit 103 is switched off when the controller 102 enters the standby mode, and the master switch circuit 103 is switched on when the controller 102 enters the operation mode. After the controller 102 enters the operation mode, the controller 102 is configured to respectively control the first switch circuit 104 and the second switch circuit 105 to be switched on or switched off according to the first switch signal and the second switch signal that are received by the controller 102. Hence, in a situation where two electric appliances (e.g., a stewing pot and a multi-functional cooker having only one pop-up switch) are placed in the flip-down electronics cabinet 900, and the multi-functional cooker has finished cooking, the switch of the multi-functional cooker will pop up, and the multi-functional cooker starts to keep the food warm. However, the stewing pot still needs to perform cooking for 4 hours to 6 hours. At this time, the user may press or touch the first switch key 1012 or the second switch key 1013 that is disposed on the control interface 101 and corresponds to the multi-functional cooker, so as to switch off the first switch circuit 104 or the second switch circuit 105. In this way, the stewing pot continues operating, but the multi-functional cooker is stopped from operating. When warming of the food is not required, the user does not need to put his/her hand into the cabinet body 1 that is full of hot air for finding and pulling out a plug, thereby significantly improving convenience and safety in use.

In one embodiment, since the plugs of the two electric appliances inside the flip-down electronics cabinet 900 are usually inserted into the sockets for a long duration (e.g., the plugs of the above-mentioned stewing pot and multi-functional cooker are respectively inserted into the first socket 91 and the second socket 92), the controller 102 is further configured to continuously record manually switched-off frequencies of the first switch circuit 104 and the second switch circuit 105, so as to automatically switch off the first switch circuit 104 or the second switch circuit 105 according to a highest one of the manually switched-off frequencies of the first switch circuit 104 and the second switch circuit 105.

Figure 5:
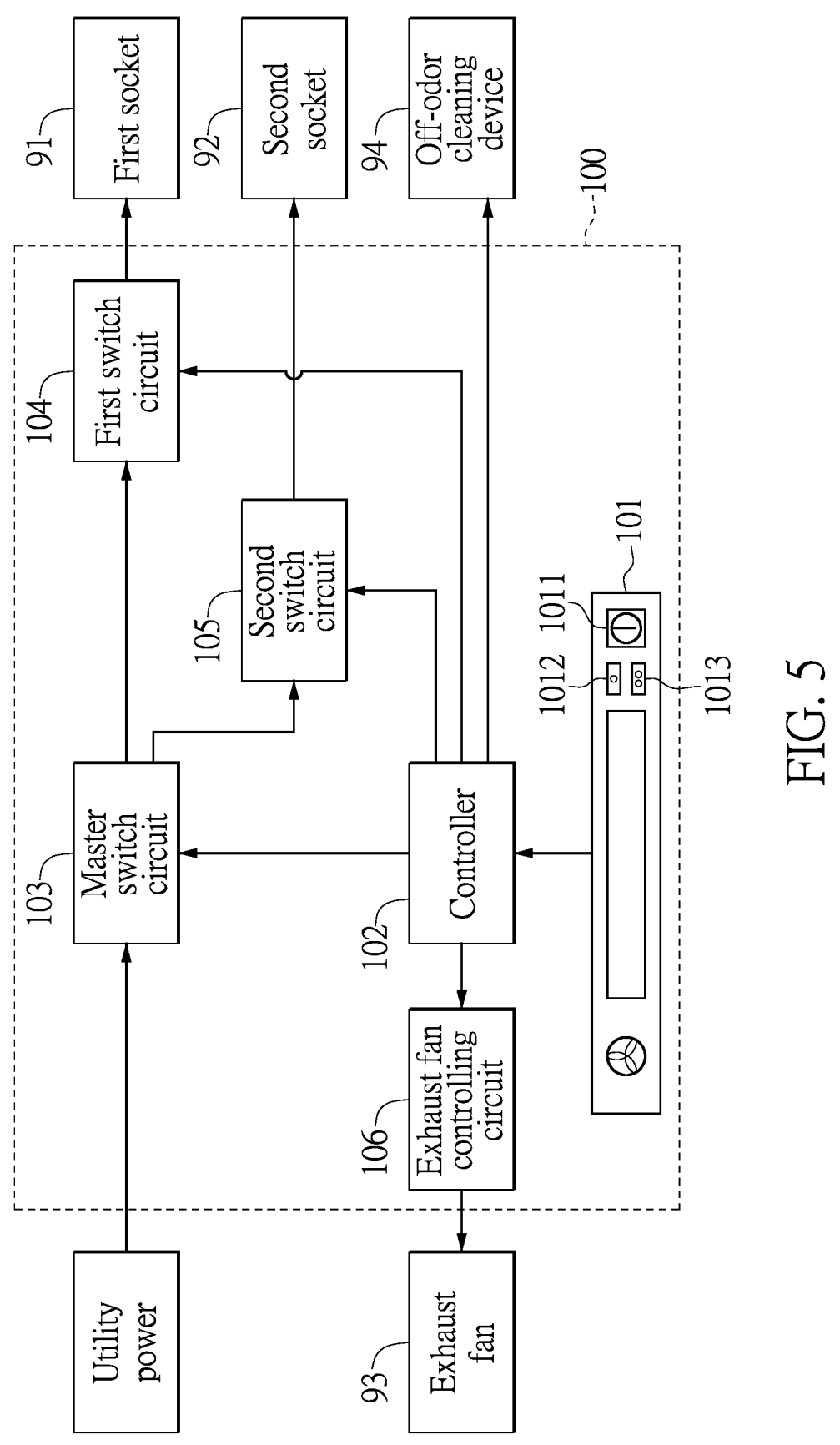
FIG. 5 is another functional block diagram of the flip-down electronics cabinet having the circuit controlling device according to the present disclosure.

Reference is made to FIG. 5. In one embodiment, an off-odor cleaning device 94 that is electrically connected to the controller 102 can be disposed on an appropriate location inside the cabinet body 1, such as on the side plates 14 or the rear plate 13. The off-odor cleaning device 94 can be a negative ion cleaning device. When the first switch circuit 104 and the second switch circuit 105 are switched off (i.e., when the controller 102 receives the first switch signal and the second switch signal to switch off the first switch circuit 104 and the second switch circuit 105), the off-odor cleaning device 94 is configured to ionize air molecules, so as to generate a large amount of negative ions and a minute amount of ozone for neutralization of an off-odor and sterilization of bacteria. Accordingly, hygiene for future use can be ensured by rapid removal of the off-odor and the bacteria in the cabinet body 1. The off-odor cleaning device 94 of the present embodiment can also be a photocatalytic ultraviolet cleaning device. When the first switch circuit 104 and the second switch circuit 105 are switched off (i.e., when the controller 102 receives the first switch signal and the second switch signal to switch off the first switch circuit 104 and the second switch circuit 105), the off-odor cleaning device 94 is configured to irradiate ultraviolet light on a photocatalyst, so as to generate oxygen-containing radicals that have a strong oxidizing property for strong oxidative decomposition of the off-odor and the bacteria. Due to combined disinfection effects of the ultraviolet light and the photocatalyst, the off-odor and the bacteria in the cabinet body 1 can be rapidly removed. Moreover, the off-odor cleaning device 94 of the present embodiment can include the above-mentioned negative ion cleaning device and photocatalytic ultraviolet cleaning device at the same time.

Figure 6:
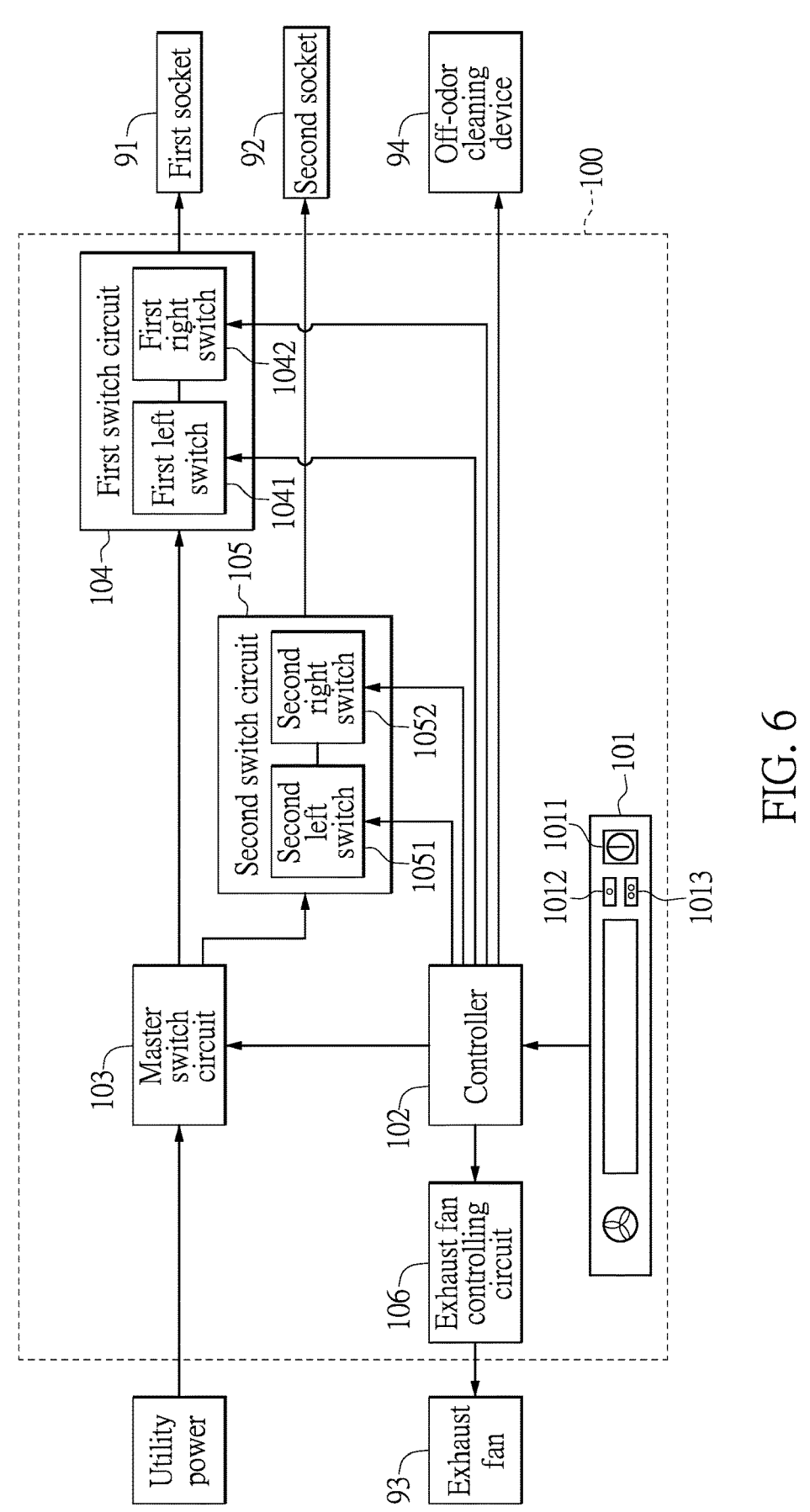
FIG. 6 is yet another functional block diagram of the flip-down electronics cabinet having the circuit controlling device according to the present disclosure.

Reference is made to FIG. 6. In one embodiment, the first switch circuit 104 includes a first left switch 1041 and a first right switch 1042 that are connected to each other. The first left switch 1041 and the first right switch 1042 are each electrically connected to the controller 102, such that an electric current can be supplied to the first socket 91 only when the first left switch 1041 and the first right switch 1042 are both switched on.

In addition, the second switch circuit 105 includes a second left switch 1051 and a second right switch 1052 that are connected to each other. The second left switch 1051 and the second right switch 1052 are each electrically connected to the controller 102, such that the electric current can be supplied to the second socket 92 only when the second left switch 1051 and the second right switch 1052 are both switched on.

In the present embodiment, the first left switch 1041 and the second left switch 1051 are semiconductor switches, and the first right switch 1042 and the second right switch 1052 are relay switches. Moreover, in order to switch the first switch circuit 104 or the second switch circuit 105 from on to off, the controller 102 is configured to quickly switch off the first left switch 1041 or the second left switch 1051, and then switch off the first right switch 1042 or the second right switch 1052. In this way, when a large electric current is supplied to the first socket 91 or the second socket 92, generation of sparks can be prevented during switching on or off of the first right switch 1042 or the second right switch 1052 (the relay switches), thereby improving stability of the overall circuit.

BENEFICIAL EFFECTS OF THE EMBODIMENTS

In conclusion, the flip-down electronics cabinet 900 provided by the present disclosure includes the cabinet body 1, the two first sliding rails 2, the two second sliding rails 3, the carrying tray 4, the door plate 5, and the circuit controlling device 100. The circuit controlling device 100 is disposed in the cabinet body 1. The circuit controlling device 100 includes the control interface 101, the controller 102, the master switch circuit 103, the first switch circuit 104, and the second switch circuit 105. The first switch circuit 104 is electrically connected between the master switch circuit 103 and the first socket 91, and the second switch circuit 105 is electrically connected between the master switch circuit 103 and the second socket 92. The control interface 101 includes the master switch key 1011, the first switch key 1012, and the second switch key 1013. The master switch key 1011 is configured to generate the master switch signal that is transmitted to the controller 102, the first switch key 1012 is configured to generate the first switch signal that is transmitted to the controller 102, and the second switch key 1013 is configured to generate the second switch signal that is transmitted to the controller 102. The controller 102 enters the operation mode or the standby mode according to the master switch signal that is received by the controller 102. The master switch circuit 103 is switched off when the controller 102 enters the standby mode, and the master switch circuit 103 is switched on when the controller 102 enters the operation mode. After the controller 102 enters the operation mode, the controller 102 is configured to respectively control the first switch circuit 104 and the second switch circuit 105 to be switched on or switched off according to the first switch signal and the second switch signal that are received by the controller 102. Therefore, the user no longer needs to put his/her hand into a cabinet body that is full of hot air for finding and pulling out the plug, such that convenience and safety in use can be significantly improved, and a long existing issue in the related art can be addressed.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A flip-down electronics cabinet, comprising:

a cabinet body including a top plate, a bottom plate, a rear plate, and two side plates, wherein a first space and a second space are formed between the top plate, the bottom plate, the rear plate, and the two side plates; wherein an opening is formed at a front side of the cabinet body, and the opening is in spatial communication with the first space and the second space; wherein a first socket and a second socket are disposed at a rear side of the cabinet body, and are each exposed from the first space;

two first sliding rails oppositely disposed on the two side plates of the cabinet body, wherein the two first sliding rails are disposed in the first space;

two second sliding rails oppositely disposed on the two side plates of the cabinet body, wherein the two second sliding rails are disposed in the second space below the first space;

a carrying tray, wherein a left side and a right side of the carrying tray are respectively disposed on the two first sliding rails;

a door plate, wherein a left side and a right side of the door plate are respectively disposed on the two second sliding rails, and opening and closing actions of the door plate are performable relative to the cabinet body; and a circuit controlling device disposed in the cabinet body, wherein the circuit controlling device includes a control interface, a controller, a master switch circuit, a first switch circuit, and a second switch circuit; wherein the controller is electrically connected to the control interface, the master switch circuit, the first switch circuit, and the second switch circuit, the first switch circuit is electrically connected between the master switch circuit and the first socket, and the second switch circuit is electrically connected between the master switch circuit and the second socket; wherein the control interface includes a master switch key, a first switch key, and a second switch key, the master switch key is configured to generate a master switch signal that is transmitted to the controller, the first switch key is configured to generate a first switch signal that is transmitted to the controller, and the second switch key is configured to generate a second switch signal that is transmitted to the controller; wherein the controller is configured to enter an operation mode or a standby mode according to the master switch signal that is received by the controller; wherein the master switch circuit is switched off when the controller enters the standby mode, and the master switch circuit is switched on when the controller enters the operation mode; wherein, after the controller enters the operation mode, the controller is configured to respectively control the first switch circuit and the second switch circuit to be switched on or switched off according to the first switch signal and the second switch signal that are received by the controller.

2. The flip-down electronics cabinet according to claim 1, wherein the first switch circuit includes a first left switch and a first right switch that are connected to each other, and the first left switch and the first right switch are each electrically connected to the controller; wherein the second switch circuit includes a second left switch and a second right switch that are connected to each other, and the second left switch and the second right switch are each electrically connected to the controller; wherein the first left switch and the second left switch are semiconductor switches, and the first right switch and the second right switch are relay switches; wherein the controller is configured to quickly switch off the first left switch or the second left switch, and then switch off the first right switch or the second right switch, such that the first switch circuit or the second switch circuit is switched from on to off.

3. The flip-down electronics cabinet according to claim 1, wherein the controller is further configured to continuously record manually switched-off frequencies of the first switch circuit and the second switch circuit, so as to automatically switch off the first switch circuit or the second switch circuit according to a highest one of the manually switched-off frequencies of the first switch circuit and the second switch circuit.

4. The flip-down electronics cabinet according to claim 1, wherein at least one exhaust fan is disposed inside the cabinet body, the circuit controlling device further includes an exhaust fan controlling circuit, and the exhaust fan controlling circuit is electrically connected between the controller and the at least one exhaust fan.

5. The flip-down electronics cabinet according to claim 1, wherein an off-odor cleaning device is disposed inside the cabinet body, and the off-odor cleaning device is electrically connected to the controller; wherein the off-odor cleaning device is a negative ion cleaning device configured to ionize air molecules when the first switch circuit and the second switch circuit are switched off, so as to generate a large amount of negative ions and a minute amount of ozone for neutralization of an off-odor and sterilization of bacteria.

6. The flip-down electronics cabinet according to claim 1, wherein an off-odor cleaning device is disposed inside the cabinet body, and the off-odor cleaning device is electrically connected to the controller; wherein the off-odor cleaning device is a photocatalytic ultraviolet cleaning device configured to irradiate ultraviolet light on a photocatalyst when the first switch circuit and the second switch circuit are switched off, so as to generate oxygen-containing radicals that have a strong oxidizing property for strong oxidative decomposition of an off-odor and bacteria.

* * * * *